US006603552B1

(12) United States Patent
Cline et al.

(10) Patent No.: US 6,603,552 B1
(45) Date of Patent: Aug. 5, 2003

(54) PORTABLE SYSTEM FOR DETECTING SKIN ABNORMALITIES BASED ON CHARACTERISTIC AUTOFLUORESCENCE

(75) Inventors: Richard W. Cline, Vancouver (CA); Pierre Leduc, Surrey (CA)

(73) Assignee: Xillix Technologies Corp., Richmond (CA)

( * ) Notice: Subject to any disclaimer, the term of this patent is extended or adjusted under 35 U.S.C. 154(b) by 0 days.

(21) Appl. No.: 09/469,562

(22) Filed: Dec. 22, 1999

(51) Int. Cl.[7] .................... G01N 33/48; G01N 21/25; A61B 5/00
(52) U.S. Cl. .................... 356/417; 356/39; 600/317
(58) Field of Search .................... 356/417, 39; 600/476, 600/477, 317

(56) References Cited

U.S. PATENT DOCUMENTS

| | | |
|---|---|---|
| 4,200,801 A | 4/1980 | Schuresko |
| 4,532,918 A | 8/1985 | Wheeler |
| 4,556,057 A | 12/1985 | Hiruma et al. |

(List continued on next page.)

FOREIGN PATENT DOCUMENTS

| | | |
|---|---|---|
| DE | 196 08 027 A1 | 9/1996 |
| EP | 0 512 965 A1 | 11/1992 |
| EP | 0 792 618 A1 | 9/1997 |
| JP | H7-155285 | 6/1995 |
| JP | H07-155286 | 6/1995 |
| JP | H07-155290 | 6/1995 |
| JP | H07-155291 | 6/1995 |
| JP | H07-155292 | 6/1995 |
| JP | 7-204156 A | 8/1995 |
| JP | H7-250804 | 10/1995 |
| JP | H07-250812 | 10/1995 |
| JP | 8-224208 | 9/1996 |
| JP | 8-224209 | 9/1996 |
| JP | 8-224240 | 9/1996 |
| JP | 10-151104 A | 6/1998 |
| JP | 10-201700 A | 8/1998 |
| JP | 10-104070 A | 4/1999 |
| JP | H11-155812 | 6/1999 |
| WO | WO 95/26673 | 10/1995 |
| WO | WO 98/24360 | 6/1998 |
| WO | WO 00/42910 | 7/2000 |

OTHER PUBLICATIONS

Alfano et al., "Fluoescence spectra from cancerous and normal human breast and lung tissues", *IEEE Journal of Quantam Electronics*, vol. QE–23, No. 10, pp. 1806–1811, 1987.

Andersson–Engels et al., "Tissue diagnostics using laser induced fluorescence", Ber. Bunsenges, *Physical Chemistry*, No. 93, pp. 335–342, 1989.

Hung et al., "Autofluorescence of normal and malignant bronchial tissue", *Lasers in Surgery and Medicine*, No. 11, pp. 99–105, 1991.

*Primary Examiner*—Zandra V Smith
(74) *Attorney, Agent, or Firm*—Christensen O'Connor Johnson Kindness PLLC

(57) ABSTRACT

A lightweight hand-held skin abnormality detection system includes a source of excitation light that causes tissue under examination to produce fluorescence light. The fluorescence light produced along with the beam of reference light is provided to a beam splitter which divides the fluorescence light and the reference light into separate optical channels. Each optical channel produces an image of the tissue under examination. A passive optical combiner superimposes the image produced by each optical channel for viewing by a user.

33 Claims, 4 Drawing Sheets

U.S. PATENT DOCUMENTS

| | | |
|---|---|---|
| 4,786,813 A | 11/1988 | Svanberg et al. |
| 4,821,117 A | 4/1989 | Sekiguchi |
| 4,930,516 A | 6/1990 | Alfano et al. |
| 5,134,662 A | 7/1992 | Bacus et al. |
| 5,165,079 A | 11/1992 | Schulz-Hennig |
| 5,214,503 A | 5/1993 | Chiu et al. |
| 5,225,883 A | 7/1993 | Carter et al. |
| 5,255,087 A | 10/1993 | Nakamura et al. |
| 5,365,057 A | 11/1994 | Morley et al. |
| 5,371,355 A | 12/1994 | Wodecki |
| 5,377,686 A | 1/1995 | O'Rourke et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,430,476 A | 7/1995 | Häfele et al. |
| 5,507,287 A | 4/1996 | Palcic et al. |
| 5,590,660 A | 1/1997 | MacAulay et al. |
| 5,647,368 A | 7/1997 | Zeng et al. |
| 5,827,190 A | 10/1998 | Palcic et al. |
| 6,008,889 A | 12/1999 | Zeng et al. |
| 6,021,344 A | 2/2000 | Lui et al. |
| 6,069,689 A | 5/2000 | Zeng et al. |
| 6,148,227 A | 11/2000 | Wagnières et al. |

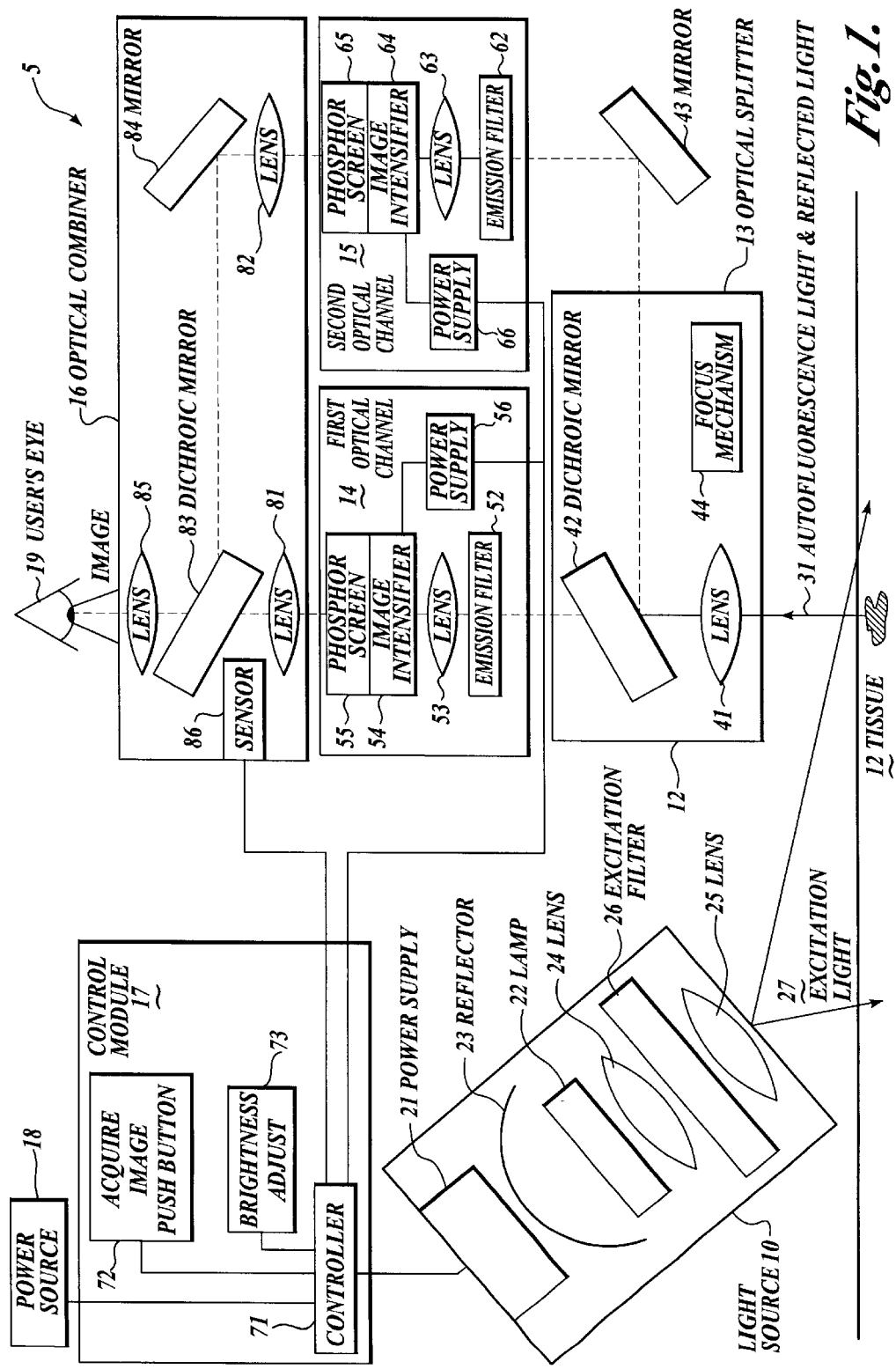

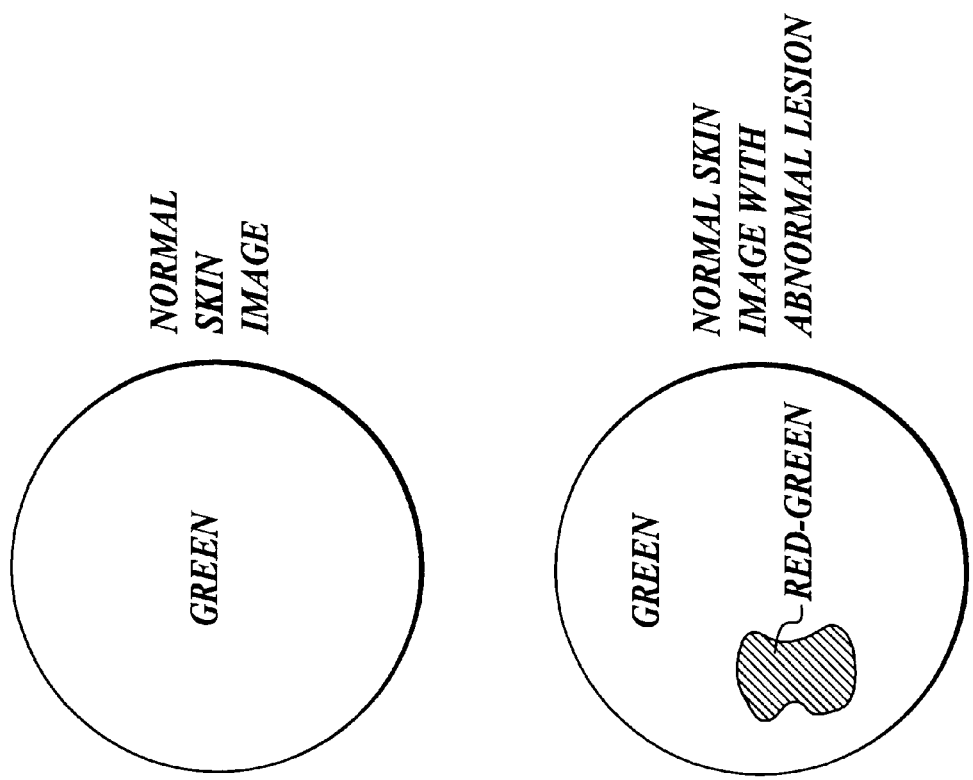

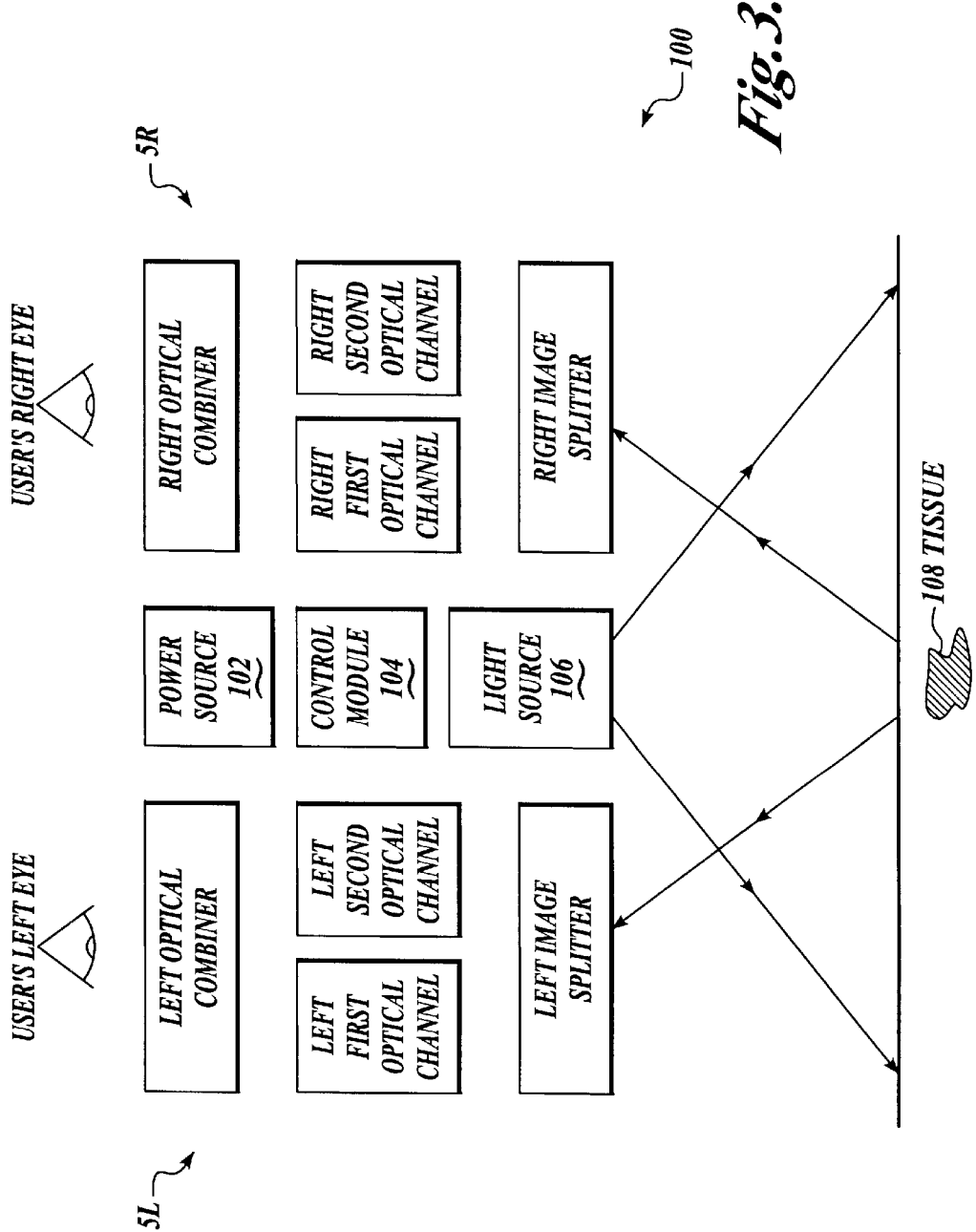

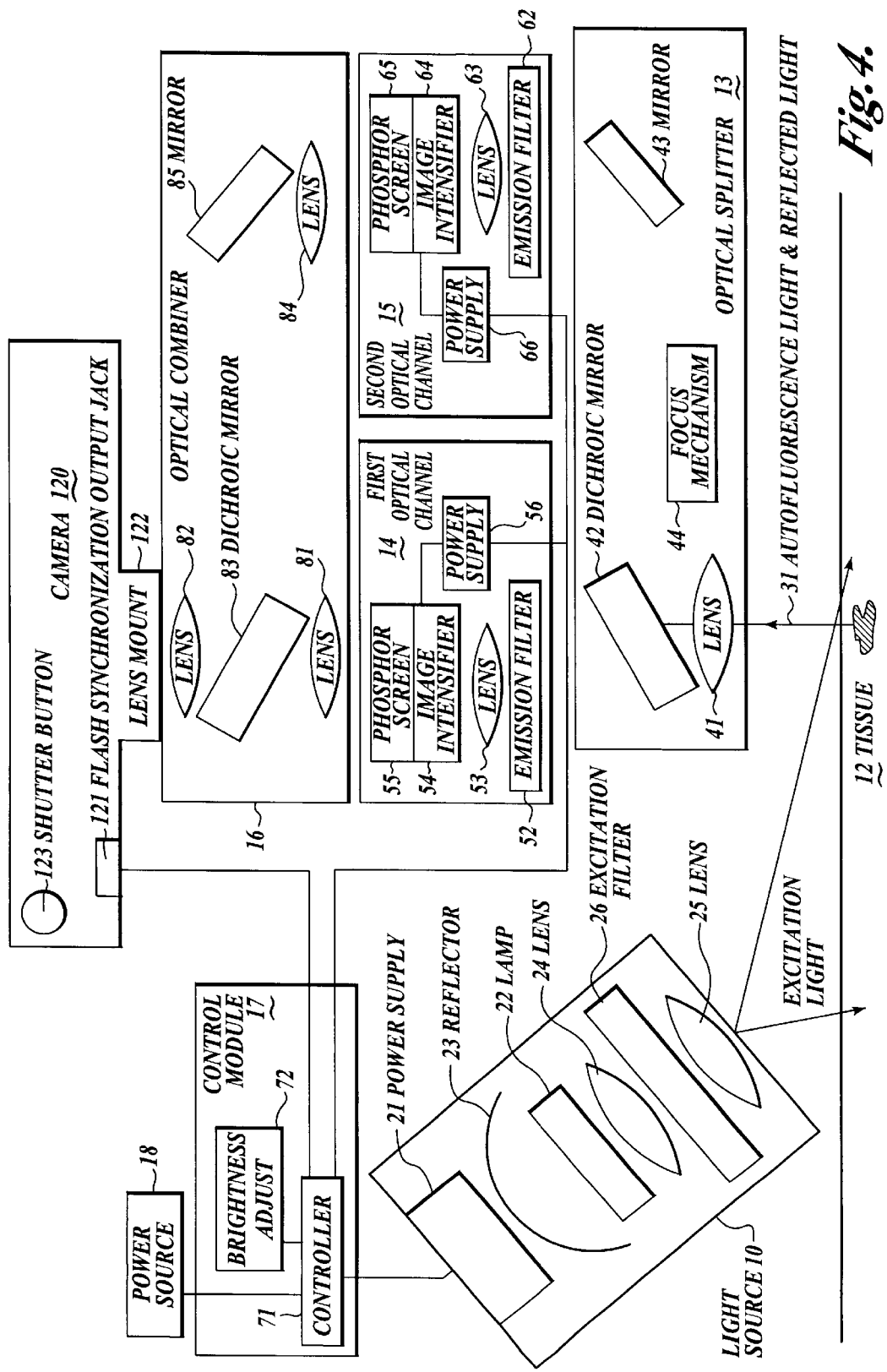

PORTABLE SYSTEM FOR DETECTING SKIN ABNORMALITIES BASED ON CHARACTERISTIC AUTOFLUORESCENCE

FIELD OF THE INVENTION

The present invention relates to the detection of skin abnormalities and, more particularly, to the detection of cancerous or precancerous skin tissue using autofluorescence.

BACKGROUND OF THE INVENTION

Whether due to increased awareness or a variety of environmental factors, the incidence of detected cases of skin cancer is increasing. Because most skin cancers are curable if treated early, there is an increased emphasis on the detection of malignant or premalignant skin tissue. The majority of skin cancers are detected based on a visual observation of a patient's skin under white light by a trained dermatologist. However, the success of such a method relies heavily on the ability of the physician to distinguish healthy skin from a potentially malignant lesion.

One technique that can aid a physician in the detection of cancerous or pre-cancerous lesions is based on the difference in autofluorescence light produced by healthy and non-healthy tissue. All tissue will fluoresce or produce light within a well-defined range of wavelengths when excited. It is known that the autofluorescence light produced by healthy tissue has a spectral profile that differs from that produced by non-healthy tissue. A number of research groups have exploited this difference in the spectral profile by recording the wavelength spectrum of a single point. Although this provides interesting data, it is clinically difficult to use.

One system for detecting cancerous tissue based on differences in autofluorescence light is described in U.S. Pat. No. 5,507,287, which is assigned to the Xillix Technologies Corporation of Richmond, B.C., Canada, the assignee of the present invention. However, this and similar systems generally require a computer monitor and image processing equipment in order to produce images of suspect tissue and are not portable enough to be used outside a hospital. In addition, these systems are relatively expensive and require significant amounts of energy to operate.

A lightweight, portable system for the detection of autofluorescence light of the skin is described in PCT application PCT/CA97/00919, entitled "Fluorescence Scope System for Dermatologic Diagnosis." However, depending on the embodiment, this device either lacks sensitivity due to the lack of light amplification, or is difficult to use due to the requirement for the user to mentally combine images of different colors presented to each eye.

To increase the ability of medical personnel to perform screening tests on greater numbers of patients, there is a need for a low-cost, lightweight, portable cancer detection system that can aid physicians in the detection of potentially malignant lesions based on differences in the autofluorescence light produced by healthy and suspect tissue.

SUMMARY OF THE INVENTION

The present invention is a lightweight, hand-held skin abnormality detection imaging system including a source of excitation light which causes tissue under examination to produce autofluorescence light. The autofluorescence light generated from the tissue under examination along with reference light is directed to a pair of optical channels that produce an image of the tissue under examination. An optical combiner, which preferably comprises a dichroic mirror, superimposes the images of the tissue to be viewed by a user.

In one embodiment of the invention, the autofluorescence light received in one channel has a wavelength selected such that the autofluorescence intensity for healthy tissue differs from the autofluorescence intensity produced for diseased or suspect tissue. The reference light comprises autofluorescence light, wherein the autofluorescence intensity for diseased tissue is substantially similar to the autofluorescence intensity for healthy tissue. In another embodiment of the invention, the reference light comprises reflected excitation light. In yet another embodiment of the invention, the reference light comprises light having wavelengths that differ from the wavelengths of the excitation light.

The combined superimposed output images may be viewed by a user or may be captured by an analog or digital camera. For viewing by a user, these embodiments can all be implemented with monocular or binocular viewing.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a schematic block diagram of a first embodiment of a skin abnormality detection system according to the present invention that detects abnormalities by providing a monocular, false color view of the skin based on two detection wavelength bands of autofluorescence light;

FIG. 2 is an example of a combined color view produced by the present invention using a blue excitation filter, a first autofluorescence optical channel with a green emission filter and a green phosphor screen and a second autofluorescence optical channel with a red emission filter and red phosphor screen;

FIG. 3 is a schematic block diagram of another embodiment of a skin abnormality detection system according to the present invention that detects abnormalities by providing a binocular, false color view of the skin based on two detection wavelengths of autofluorescence light; and FIG. 4 is a schematic block diagram of yet another embodiment of a skin abnormality detection system according to the present invention that detects abnormalities by providing a camera which captures a false color image of the skin based on two detection wavelengths of autofluorescence light.

DETAILED DESCRIPTION OF THE PREFERRED EMBODIMENT

The present invention is a lightweight, hand-held system for detecting skin abnormalities based on the differences in autofluorescence light produced by healthy and diseased tissue.

As shown in FIG. 1, a skin abnormality detection system 5 according one embodiment of the present invention is made up of seven major subsystems: a light source 10 that produces excitation light that will cause a tissue sample 12 under examination to produce characteristic autofluorescence light. An optical splitter 13 divides the fluorescence light received from the tissue sample 12 into two beams of different wavelengths. The first beam is directed into a first optical channel 14 that collects, amplifies, and images the light in one fluorescence wavelength band, and a second beam is directed into a second optical channel 15 that collects, amplifies, and images the light in a second fluorescence wavelength band. An optical combiner 16 combines the images from the two optical channels 14 and 15 into one and presents the combined image the user's eye 19. In addition, the system 10 includes a control module 17, and a power source 18. The system described above is a monocular viewer that produces a combined false color image that is made up of images from two fluorescence wavelength bands.

The power source 18 could be batteries or the AC line. In the preferred embodiment battery power is utilized for portability.

The light source 10 provides light of the required characteristics for exciting the tissue fluorescence. It consists of a power supply 21, which is controlled by the control module 27 and which receives electrical power from power source 18. The power supply outputs electrical power of the appropriate characteristics to operate a lamp 22. The lamp, which may be a xenon flash lamp, produces a broad spectrum output of visible light (e.g. white light). The light is formed into a beam which uniformly illuminates the tissue 12 by a reflector 23 and the combination of image forming elements 24 and 25 (e.g. lenses). A region of collimated light is produced between the two lenses. The region of collimated light provides optimal conditions for the placement of an optical band pass filter, excitation filter 26, designed for incident light to be perpendicular to filter's surface. The excitation filter characteristics are preferably selected such that the filter passes light of wavelengths utilized to excite fluorescence (typically 400 nm to 450 nm) and blocks light of other wavelengths. The blocking by the filter in the wavelength bands where fluorescence is detected must be very good (i.e. in those bands, less than 1 in $10^5$ of the light from the lamp should be able to pass through the filter).

Typically, the lamp 22 is operated in a pulsed mode similar to a camera flash; however, it could be on continuously. The advantages of operating in the pulsed mode are that it allows the system to be utilized in an undarkened room and the power required is reduced so battery operation is possible. The intensity and duration of the light (when pulsed) are controlled by the control module 17 as a means of adjusting the brightness of the image as detected by the user's eye 19.

The result of illuminating the tissue 12 with excitation light is the emission of characteristic autofluorescence light 31 by the tissue. If the excitation light is in the blue portion of the spectrum, the emitted fluorescence typically spans wavelengths from the green to the red (470 nm to 700 nm). The emitted autofluorescence light 31 is collected and split into two wavelength bands by the optical splitter 13. An image forming element (e.g. lens assembly) 41 in the optical splitter 13 collects the emitted fluorescence light and forms an image of the tissue at infinity. The image can be focused at infinity via focus mechanism 44. The light is directed onto a dichroic mirror 42 resulting in the autofluorescence light being split into two wavelength bands. A portion of the light in one wavelength band passes straight through the dichroic mirror 42 and enters the first optical channel 14. The remaining light in the second wavelength band is reflected by the dichroic mirror 42. Typically, the dichroic mirror 42 will pass light having wavelengths less than 570 nm and will reflect light having wavelengths greater than 570 nm. The light reflected by the dichroic mirror is again reflected by a mirror 43 into the second optical channel 15.

As mentioned previously, the autofluorescence light that passes straight through the dichroic mirror 42 enters the first optical channel 14. In this optical channel, autofluorescence light with wavelengths within a defined band is amplified and formed into an image. The optical channel 14 consists of an emission filter 52, a lens assembly 53, an image intensifier 54 with phosphor screen 55 and power supply 56. Emission filter 52 passes only the autofluorescence light in a band of wavelengths near the maximum in the tissue spectral emission (typically 490 nm to 560 nm). The emission filter 52 should have particularly good blocking characteristics for light in the wavelength band utilized for fluorescence excitation-typically less than 1 in $10^5$ of the excitation light passes the emission filter 52. The lens 53 forms an image with the autofluorescence light on the input of the image intensifier 54. The image intensifier is a device that amplifies the light by a gain determined by a bias voltage that is supplied by power supply 56. The image intensifier produces an output image on a phosphor screen 55 (actually an integral part of the image intensifier). The power supply 56 is controlled by a controller 71 within the control module 17. The controller 71 controls the output of the power supply 56 in such a way that the intensifier has the appropriate gain for the light input into the system and is protected from overexposure. The image intensifier phosphor screen 55 preferably has a long persistence so that the amplified image would be visible for a few seconds. The phosphor screen 55 would produce light of a specific wavelength band, for example green light mainly in the band 500 nm to 560 nm. The light from the image on the phosphor screen 55 is input to the optical combiner 16.

As mentioned previously, the autofluorescence light that is reflected by the dichroic mirror 42 and mirror 43 in the optical splitter 13 enters into the second optical channel 15. The second optical channel 15 consists of an emission filter 62, a lens 63, an image intensifier 64 with phosphor screen 65 and power supply 66. The second optical channel 15 is nearly identical to the first optical channel 14 except that the emission filter 62 is different than emission filter 52 in that filter 62 passes light of a different wavelength band (e.g. passes red light in the band 630 to 750 nm). The phosphor screen 65 produces light of a different wavelength (e.g. produces red light in the band 620 nm to 700 nm) than the phosphor screen 55 does with long persistence, and the gain of the image intensifier 64 as set by the controller 71 and power supply 66 may be different than the gain of image intensifier 54. As a result of these differences, the image formed on phosphor screen 65 is from a different autofluorescence band and may be of different brightness. The light from the image on phosphor screen 65 is supplied as an input to the optical combiner 16.

The optical combiner 16 consists of a lens 81, a lens 82, a dichroic mirror 83, a mirror 84, a lens 85, and a light sensor 86. The lens 81 collects light from the image on phosphor screen 55, and in combination with lens 85 relays the image from the phosphor screen to the user's eye 19. Light from the image on phosphor screen 55 in one wavelength band (e.g. green light) passes straight through dichroic mirror 83. The dichroic mirror 83 has, for example, characteristics such that light at wavelengths shorter than 570 nm passes straight through and light at wavelengths longer than 570 nm is reflected. Lens 82 collects light from the second optical channel in a second wavelength band (e.g. red light) from the image on phosphor screen 65. Lens 82, in combination with lens 85 relays the image from phosphor screen 65 to the user's eye 19. The light from phosphor screen 65 is reflected both by mirror 84 and dichroic mirror 83. This results, in combination with the image from phosphor screen 55 that passed straight through the dichroic mirror 83, in the formation of a combined image a the user's eye 19 made up of the images from phosphor screens 55 and 65. The magnifications of lenses 81 and 82 are chosen so that the images from phosphor screens 55 and 65 are the same size at the user's eye, even though the optical path lengths are different.

In addition to passing straight through dichroic mirror 83, a small proportion of the light from phosphor screen 55 is reflected by the dichroic mirror (typically 5%) onto sensor 86. This light is converted into an electrical signal proportional to the light amplitude, which is measured by the control module 17.

The control module 17 consists of the controller 71, acquire image pushbutton 72, and brightness adjustment knob 73. The controller 71 contains circuitry to control the light source power supply 21 and image intensifier power supplies 56, 66, as well as, circuitry that measures the output voltage of light sensor 86. The acquire image pushbutton 72 is activated by the user to signal to the controller to start the image acquisition sequence when the device is operated in a pulsed mode.

The brightness adjustment knob 73 is utilized by the user to communicate an adjustable reference point for the brightness of the image to the controller. The brightness of the image seen by the user is automatically controlled by the controller 71 based on a combination of measurement of light intensity by the light sensor 86, the reference brightness from the brightness adjustment knob 73, and stored image intensifier calibration characteristics. The controller 71 utilizes this information to control the light source intensity and duration, as well as the gain of image intensifiers 54 and 64. In order to achieve the best image quality, the control algorithm is designed to operate at the maximum possible light source intensity and pulse duration and minimum intensifier gains. The control algorithm first adjusts the light source intensity and duration (when pulsed) to achieve the desired brightness. The algorithm then adjusts the gain of image intensifier 54 to achieve the target brightness and then adjusts the gain of image intensifier 64 in such a way that the ratio of the gain of intensifier 54 to the gain of intensifier 64 is constant, based on the calibration parameters. In this way, the color of the combined image is made to be independent of the brightness of the image and independent of the distance between the tissue and the device.

Using the system 5 described above, two images of different color and brightness originating from two autofluorescence wavelength bands are overlaid for interpretation by the user as illustrated in FIG. 2. The color of the resulting combined image depends on the degree of abnormality of the tissue. The spectral characteristics of autofluorescence light emitted by the tissue depend on the degree of abnormality. Typically the autofluorescence light emission of abnormal tissue is different in the green portion of the spectrum compared to normal tissue. In contrast, the autofluorescence light emission in the red portion of the spectrum is essentially unchanged when comparing abnormal and normal tissue. As a result, the brightness of the green component of the combined image varies, depending on the degree of tissue abnormality. Tissue with a degree of abnormality appears a different shade (redder or greener) than normal tissue. Typically, users can easily discern subtle color differences indicative of abnormal tissue, especially when one area in the field of view is different than the rest.

A second embodiment of the skin abnormality detection system is also based on FIG. 1. The architecture of the system is the same as the first embodiment and a combined view similar to that shown in FIG. 2 is produced, but a different principle of operation is utilized, necessitating different implementation details. In the first embodiment, an image is produced by overlaying images from two different wavelength bands of autofluorescence light. The color of the composite image resulting from the first embodiment depends on the health of the tissue, because the intensity of the autofluorescence light forming one of the images (green) is known to be a strong function of the health of the tissue, whereas the intensity of autofluorescence light forming the second image (red) depends weakly on the health of the tissue. In the second embodiment, a composite image is formed based on one image from the wavelength band of autofluorescence light that is a strong function of the health of the tissue (green), and one image formed from reflected excitation light (blue). As in the first embodiment, the color of the combined image depends on the health of the tissue, because the intensity of the autofluorescence light forming one image utilized in the composite varies depending on the health of the tissue, whereas the intensity of the reflected light forming the second image of the composite depends only weakly on the health of the tissue.

The implementation details for the second embodiment are different from those of the first embodiment in the following ways: The emission filter 62 for the second optical channel 15 transmits light reflected from the tissue of the same wavelength band as the light emitted by the light source (e.g. 400 nm to 450 nm). In addition, because the reflected light is of much stronger intensity than the fluorescence light utilized in the first embodiment, the image intensifier 64 in the second optical channel 15 of the second embodiment does not need to amplify the light as much and can be of lower quality. Note that, although dichroic mirror 42 is designed to transmit light with shorter wavelengths, for example <570 nm in the first embodiment, there is no need to utilize a different dichroic mirror for the second embodiment. This is because dichroic mirrors typically reflect 5% of the incident light in region they transmit, so the dichroic mirror 42 specified in the first embodiment can be utilized to reduce the intensity of the light reflected from the tissue going into the second optical channel 15. Alternatively, a dichroic mirror that transmits in the green and reflects in the blue (e.g. reflects wavelengths <470 nm and transmits wavelengths >470 nm) in conjunction with a neutral density filter or low gain image intensifier can be utilized.

Like the second embodiment, a third embodiment of the skin abnormality detection system is also based on the architecture of FIG. 1 and produces a combined view similar to that shown in FIG. 2. The third embodiment utilizes the same principle of operation as the second embodiment, but differs in the implementation details. Like the second embodiment, a combined image is formed from the combination of a fluorescence image and a reflected image. The difference is that instead of utilizing the excitation light as the source of light for the reflected image, the light source 10 outputs light expressly for the purpose of producing a reflected image, at a wavelength that is longer than that utilized for the detection of fluorescence. To produce light both at the wavelength required for the excitation of fluorescence and for the purpose of producing a long wavelength reflected image, the excitation filter 26 in the third embodiment has two passbands, one passing short wavelengths for fluorescence excitation (for example 400 nm to 450 nm), and one passing longer wavelengths for the reflected image (for example 630 nm to 700 nm). The filter preferably has very good blocking characteristics in the wavelength region where fluorescence is detected (e.g. less than $10^{-5}$ of the incident light should be transmitted between 470 nm and 600 nm). The emission filter 62 passes light in the longer wavelength band which is used for the reflected image (for example 630 nm to 700 nm). This filter 62 should have good blocking of the light in the excitation wavelength band (400 nm to 450 nm in this example). The emission filter 52 must, in addition to the characteristics described for the first embodiment, also have good blocking of light in the band used for the reflect image (for example, in the band 630 nm to 700 nm less than $10^5$ of the light should pass the filter). The balance of the system is similar to that of the second embodiment.

A fourth embodiment of the skin abnormality detection system according to the present invention is shown in FIG. 3. The fourth embodiment is a viewer that produces a combined, binocular image based on images either from two wavelength bands of emitted autofluorescence light, or from one wavelength band of emitted autofluorescence light and one wavelength band of reflected light. The system described in the fourth embodiment can be obtained by combining two of the systems (ie., one for each eye) described in one of the first three embodiments to obtain a binocular view. In the example shown in FIG. 3, the imaging system 100 includes a power source 102, a control module 104 and a fight source 106 that supplies light to excite a tissue sample 108 to produce autofluorescence light. A left imaging system 5L provides a superimposed autofluorescence image to a viewer's left eye in the same manner as the system shown in FIG. 1 and described above. An imaging system 5R provides a superimposed autofluorescence image for a viewer's right eye in the same manner as the system 5 shown in FIG. 1.

A fifth embodiment of the skin abnormality detection system is shown in FIG. 4. The fifth embodiment is an optical system that produces a combined image based on images from two wavelength bands of emitted autofluorescence light. The fifth embodiment is similar to the first embodiment, except that it is intended to be utilized with an instant camera or a digital camera instead of the user's eye. A combined view, similar to that shown in FIG. 2 is recorded and displayed by means of the camera.

As shown in FIG. 4, the fifth embodiment of a skin abnormality detection system according to the present invention is made up of eight major subsystems: a light source 10 that produces excitation light that will cause the tissue 12 under examination to produce characteristic autofluorescence light, an optical splitter 13 that divides the fluorescence light received from the tissue into two beams, a first optical channel 14 that collects, amplifies, and images the light in one fluorescence wavelength band, a second optical channel 15 that collects, amplifies, and images the light in a second fluorescence wavelength band, an optical combiner 16 that combines the images from the two fluorescence optical channels into one and presents the combined image to a digital or instant camera 120 which records the image for viewing, a control module 17, and a power source 18.

The power source 18 could be batteries or the AC line. In the preferred embodiment, battery power is utilized for portability.

The light source 10 provides light of the required characteristics for exciting the tissue fluorescence. It consists of a power supply 21 which is controlled by the control module 17 and which receives electrical power from power source 18. The power supply outputs electrical power of the appropriate characteristics to operate lamp 22. The lamp, which may be a xenon flash lamp, produces a broad spectrum output of visible light (e.g. white light). The light is formed into a beam onto the tissue 12 by reflector 23 and the combination of image forming elements 24 and 25 (e.g. lenses). In addition to forming a beam, a region of collimated light is produced between the two lenses that provides optimal conditions for the placement of an optical band pass filter, excitation filter 26. This filter 26 is designed for incident light to be perpendicular to the filter surface. The excitation filter 16 characteristics are such that the filter passes light of wavelengths utilized to excite fluorescence (typically 400 nm to 450 nm) and blocks light of other wavelengths. It is important that the filter block light in the wavelength bands where fluorescence is detected (i.e. in those bands no more than 1 in $10^5$ of the light from the lamp can pass the filter).

Typically, the lamp 22 is operated in a pulsed mode similar to a camera flash. The advantages of operating in the pulsed mode are that it allows the system to be utilized in an undarkened room and the power required is reduced so battery operation is possible. The intensity and duration of the light (when pulsed) are controlled by the control module 17 as a means of adjusting the brightness of the image as detected by the camera 120.

The result of illuminating the tissue 12 with excitation light is the emission of characteristic autofluorescence light 31 by the tissue. If the excitation light is in the blue, the emitted fluorescence typically spans wavelengths from the green to the red (470 nm to 700 nm). The emitted autofluorescence light 31 is collected and split into two wavelength bands by the optical splitter 13. An image forming element (e.g. lens) 41 in the optical splitter collects the emitted fluorescence light and forms an image of the tissue. The position of the lens 41 can be moved via focus mechanism 44 to focus the image. The light is directed onto a dichroic mirror 42 resulting in the autofluorescence light being split into two wavelength bands. A portion of the light in one wavelength band passes straight through the dichroic mirror and enters the first optical channel 14. The remaining light in the second wavelength band is reflected by the dichroic mirror 42. Typically, the dichroic mirror 42 will pass light having wavelengths less than 570 nm and will reflect light having wavelengths greater than 570 nm. The light reflected by the dichroic mirror is again reflected by a mirror 43 into the second optical channel 15.

As mentioned previously, the autofluorescence light that passes straight through the dichroic mirror 42 enters the first optical channel 14. In this optical channel, autofluorescence light with wavelengths within a defined band is amplified and formed into an image. The optical channel 14 consists of a lens 53, an emission filter 52, an image intensifier 54 with phosphor screen 55 and power supply 56. The lens 53 forms an image at an infinite distance to collimate the light. This results in an optimum location for the emission filter 52 that is designed to filter incident light perpendicular to the filter's surface. Emission filter 52 passes only the autofluorescence light in a band of wavelengths near the maximum in the tissue spectral emission (typically 490 nm to 560 nm). The emission filter preferably has good blocking characteristics for light in the wavelength band utilized for fluorescence excitation. Typically less than 1 in $10^5$ of the excitation light passes the emission filter. The lens 53 forms an image with the autofluorescence light on the input of the image intensifier 54. The image intensifier amplifies the incoming light by a gain determined by a bias voltage supplied by power supply 56. The image intensifier produces an output image on phosphor screen 55. The power supply 56 is controlled by the control module 17. The control module controls the output of the power supply in such a way that the intensifier has the appropriate gain for the light input to the system. The image intensifier phosphor screen 55 has a persistence of at least a few milliseconds, and produces light of a specific wavelength, for example green light mainly in the band 500 nm to 560 nm. The light from the image on the phosphor screen is input to the optical combiner 16.

As mentioned previously, the autofluorescence light that is reflected by the dichroic mirror enters into the second optical channel 15. The second optical channel 15 consists of a lens 63, an emission filter 62, an image intensifier 64 with phosphor screen 65 and power supply 66. The second optical channel 15 is nearly identical to the first optical channel 14 except that the emission filter 62 is different than emission filter 52 in that filter 62 passes light of a different wavelength band (e.g. red light in the band 630 to 750 nm), phosphor screen 65 produces light of different wavelength (e.g. red light in the band 620 nm to 700 nm) than phosphor screen 55, and the gain of the image intensifier 64 as set by controller 71 and power supply 66 may be different than the gain of image intensifier 54. As a result of these differences, the image formed on phosphor screen 65 is from a different autofluorescence band and may be of different brightness. The light from the image on phosphor screen 65 is input to the optical combiner 16.

The optical combiner 16 consists of lens 81, lens 82, dichroic mirror 83, mirror 84 and lens 85. Lens 81 collects light from the image on phosphor screen 55, and in combination with lens 85 relays the image from the phosphor screen to the camera's 120 optical system. Light from the image on phosphor screen 55 in one wavelength band (e.g. green light) passes straight through dichroic mirror 83. The dichroic mirror 83 has, for example, characteristics such that light at wavelengths shorter than 570 nm passes straight through and light at wavelengths longer than 570 nm is reflected. Lens 82 collects light from the second optical channel in a second wavelength band (e.g. red light) from the image on phosphor screen 55. Lens 82, in combination with lens 85 relays the image from phosphor screen 65 to the camera's 120 optical system. The light from phosphor. screen 65 is reflected both by mirror 84 and dichroic mirror 83. This results, in combination with the image from phosphor screen 55 that passed straight through the dichroic mirror 83, in the formation of a combined image appropriate for the camera's 120 optical system made up of the images from phosphor screens 55 and 65. The magnifications of lenses 81 and 82 are chosen so that the images from phosphor screens 55 and 65 are the same size at the camera's optical system, even though the optical path lengths are different.

The fifth embodiment of a skin abnormality detection system attaches to a digital or instant camera 120 by means of the camera lens mount 122, or by means of a screw in filter mount on the camera's lens.

The control module 17 consists of a controller 71, and brightness adjustment knob 72. The controller 71 contains circuitry to control the light source power supply and image intensifier power supplies. The shutter button 123 on the camera is activated by the user to start the image acquisition sequence. The camera sends a signal to the controller 71 through the flash synchronization output jack 121 indicating that image acquisition is to start and related to the image brightness. The controller makes use of this signal in controlling the light source power supply and image intensifier power supplies as described below. The brightness adjustment knob 72 is utilized by the user to communicate an adjustable reference point for the brightness of the image to the controller.

The brightness of the image as seen by the user is automatically controlled by the controller 71 based on a combination of measurement of light intensity by the camera light meter, the reference brightness from the brightness adjustment knob 72, and stored image intensifier calibration characteristics. The controller 71 utilizes this information to control the light source intensity and duration, as well as the gain of image intensifiers 54 and 64. The image intensifiers, -controlled through their power supplies, are turned on by the controller 71 only during the period that the light source outputs light, plus an additional period while the fluorescence decays (typically 100 microseconds). The camera's shutter is opened for a time much longer than the duration of the light source output (typically $\frac{1}{125}$ of a second). In order to achieve the best image quality, the control algorithm is designed to operate at the maximum possible light source intensity and pulse duration and minimum intensifier gains. The control algorithm first adjusts the light source intensity and duration to achieve the desired brightness as indicated by the camera light meter. Following this the algorithm adjusts the gain of image intensifier 54 as further required to achieve the desired brightness and then adjusts the gain of image intensifier 64 in such a way that the ratio of the gain of intensifier 54 to the gain of intensifier 64 is constant, based on the calibration parameters. In this way, the color of the combined image is made to be independent of the brightness of the image and independent of the distance between the tissue and the device.

A sixth embodiment of the skin abnormality detection system is also based on the embodiment shown in FIG. 4. The architecture of the system is the same as the fifth embodiment and a combined view similar to that shown in FIG. 2 is produced, but a different principle of operation is utilized, necessitating different implementation details. The sixth embodiment is similar to the second embodiment except that the sixth embodiment utilizes a camera to store the image whereas the second embodiment is a viewer. In the fifth embodiment, an image is produced by overlaying images from two different wavelength bands of autofluorescence light. The color of the composite image resulting from the first embodiment depends on the health of the tissue, because the intensity of the autofluorescence light forming one of the images (green) is known to be a strong function of the health of the tissue, whereas the intensity of autofluorescence light forming the second image (red) depends weakly on the health of the tissue. In comparison, in this sixth embodiment a composite image is formed based on one image from the wavelength band of autofluorescence light that is a strong function of the health of the tissue (green), and one image formed from reflected excitation light (blue). As in the fifth embodiment, the color of the combined image depends on the health of the tissue, because the intensity of the autofluorescence light forming one image utilized in the composite varies depending on the health of the tissue, whereas the intensity of the reflected light forming the second image of the composite depends only weakly on the health of the tissue.

The implementation details for the sixth embodiment are different from those of the fifth embodiment in the following ways: The emission filter 62 for the second optical channel transmits light reflected from the tissue of the same wavelength band as the light emitted by the light source (e.g. 400 nm to 450 nm). In addition, because the reflected light is of much stronger intensity than the fluorescence light utilized in the first embodiment, the image intensifier 64 in the second optical channel 15 of the second embodiment does not need to amplify the light as much and can be of lower quality. Note that, although dichroic mirror 42 is designed to transmit light with shorter wavelengths, for example <570 nm in the first embodiment, there is no need to utilize a different dichroic mirror in this embodiment. This is because typically dichroic mirrors reflect 5% of the incident light in region they transmit, so the dichroic mirror as specified in the fifth embodiment can be utilized to reduce the intensity of the light reflected from the tissue going into the second optical channel 15. Alternatively, a dichroic mirror that transmits in the green and reflects in the blue (e.g. reflects wavelengths <470 nm and transmits wavelengths >470 nm) in conjunction with a neutral density filter or low gain image intensifier can be utilized.

Like the sixth embodiment, a seventh embodiment of the skin abnormality detection system is also based on the architecture of FIG. 4 and produces a combined view similar to that shown in FIG. 2. The seventh embodiment utilizes the same principle of operation as the sixth embodiment, but differs in the implementation details. The seventh embodiment is similar to the third embodiment except that the seventh embodiment utilizes a camera to store the image whereas the third embodiment is a viewer. Like the sixth embodiment, a combined image.is formed from the combination of a fluorescence image and a reflected image. The difference is that instead of utilizing the excitation light as the source of light for the reflected image, the light source 10 outputs light expressly for the purpose of producing a reflected image, at a wavelength longer than that utilized for the detection of fluorescence. To produce light both at the wavelength required for the excitation of fluorescence and for the purpose of producing a long wavelength reflected image, the excitation filter 26 in the seventh embodiment light source has two passbands, one passing short wavelengths for fluorescence excitation (for example 400 nm to 450 nm),. and one passing longer wavelengths for the reflected image (for example 630 nm to 700 mn). The filter preferably has very good blocking characteristics in the wavelength region where fluorescence is detected (e.g. less than $10^{-5}$ of the incident light should be transmitted between 470 nm and 600 nm). The emission filter 62 must also pass light in the longer wavelength band which is used for the reflected image (for example 630 nm to 700 nm). This filter should have good blocking of the light in the excitation wavelength band (400 nm to 450 nm in this example). The emission filter 52 must, in addition to the characteristics described for the fifth embodiment, also have good blocking of light in the band used for the reflect image (for example, in the band 630 nm to 700 nm less than $10^{-5}$ of the light should pass the filter). The balance of the system is similar to that of the sixth embodiment.

While the preferred embodiment of the invention has been illustrated and described, it will be appreciated that various changes can be made therein without departing from the spirit and scope of the invention. For example, the present invention is not limited to the detection of skin cancer but can be used to detect other types of lesions that exhibit variations in autofluorescence intensities. The invention may also be utilized in internal organs such as the mouth or during surgical procedures. In addition, the abnormality detection may also be coupled to a scope, such as an endoscope or laproscope, used in the medical field to examine internal tissues and organs. The embodiments described may also be used with tissue where photodynamic agents, which enhance the fluorescence response, have been introduced. Finally, the detection system may be used not only on skin, but also on other surfaces, such as the detection of abnormalities on plants, and the detection of contaminants on non-living surfaces, such as surgical tools or food. It is, therefore, intended that the scope of the invention be determined from the following claims and equivalents thereto.

The embodiments of the invention in which an exclusive property or privilege is claimed are defined as follows:

1. A skin abnormality detection system, comprising:
   a light source for producing a concentrated beam of illumination light;
   an optical excitation filter that receives the illumination light and creates excitation light by passing light having selected wavelengths, the excitation light generating reflected and fluorescence light when directed onto a surface of interest;
   an optical splitter that receives the reflected and fluorescence light from the surface of interest and splits the fluorescence light into two wavelength bands;
   a pair of optical channels that receive the light from the optical splitter, each optical channel including:
      an optical emission filter for passing light having selected wavelengths;
      an optical assembly for forming an image of the surface of interest; and
      an image intensifier tube with a long persistence phosphor screen that amplifies the light passed by the optical emission filter and produces an output image with the light passed; and
   a passive optical combiner that receives the output image produced in each optical channel and superimposes the output images to create a combined image that is seen by a user.

2. The skin abnormality detection system of claim 1, wherein the passive optical combiner comprises a dichroic mirror that is positioned to direct the output image from each optical channel into an eye of a user.

3. The skin abnormality detection system of claim 1, further comprising a camera positioned to capture the combined output image onto an image sensor.

4. The skin abnormality detection system of claim 3, wherein the image sensor is photographic film.

5. The skin abnormality detection system of claim 3, wherein the image sensor is a digital imaging sensor.

6. The skin abnormality detection system of claim 1, wherein the system includes a pair of optical splitters which direct the light into multiple optical channels and produces a pair of combined output images for a binocular viewing.

7. A skin abnormality detection system comprising:
   a light source for producing a beam of illumination light;
   an optical excitation filter that receives the illumination light and creates excitation light and reference light, the excitation light generating fluorescence light when directed onto a surface of interest;
   an optical splitter that receives the fluorescence light and reflected reference light and directs the fluorescence light and reflected reference light into separate optical channels, each optical channel producing an image of the surface of interest; and
   a passive optical combiner that combines the images of the tissue produced with the fluorescence light and the reference light into a single image that can be viewed by a user.

8. The skin abnormality detection system of claim 7, wherein the reference light comprises the excitation light.

9. The skin abnormality detection system of claim 7, wherein the light source produces both excitation light and reference light, and the reference light comprises light having a different wavelength than the excitation light.

10. The skin abnormality detection system of claim 7, wherein the system includes a pair of optical splitters which direct the light into multiple optical channels and produces a pair of combined output images for binocular viewing.

11. The skin abnormality detection system of claim 7, further comprising a camera positioned to capture the combined output image onto an image sensor.

12. The skin abnormality detection system of claim 11, wherein the image sensor is photographic film.

13. The skin abnormality detection system of claim 11, wherein the sensor is a digital imaging sensor.

14. A tissue abnormality detection system, comprising:
   a light source for producing a concentrated beam of illumination light;
   an optical excitation filter that receives the illumination light and creates excitation light by passing light having selected wavelengths, the excitation light generating reflected and fluorescence light when directed onto a surface of interest;
   an imaging device including:
      at least one image forming optical assembly;
      an optical splitter that receives the reflected and fluorescence light from the surface of interest and splits the fluorescence light into two optical channels transmitting different wavelength bands;
      a pair of optical channels that receive the light from the optical splitter, each optical channel including:
         an optical emission filter for passing light having selected wavelengths; and
         an image intensifier tube that amplifies the light passed by the optical emission filter and produces an output image with the light passed;
      a passive optical combiner that receives the output image produced in each optical channel and superimposes the output images to create a combined image that is seen by a user; and
      a control module that controls the operation of the light source and the image intensifier tubes.

15. The tissue abnormality detection system of claim 14, wherein the optical combiner comprises a dichroic mirror that is positioned to direct the output image from each optical channel in an eye of a user.

16. The tissue abnormality detection system of claim 14, wherein the image intensifier tube have long persistence phosphor screens.

17. The tissue abnormality detection system of claim 14, further comprising a camera positioned to capture the combined output image onto an image sensor.

18. The tissue abnormality detection system of claim 17, wherein the image sensor is photographic film.

19. The tissue abnormality detection system of claim 17, wherein the image sensor is a digital imaging sensor.

20. The tissue abnormality detection system of claim 14, wherein the system includes a pair of optical splitters which direct the light into multiple optical channels and produces a pair of combined output images for a binocular viewing.

21. The tissue abnormality detection system of claim 14, wherein the light source and image intensifier tubes are operated in a pulsed mode, synchronized and controlled by the control module.

22. The tissue abnormality detection system of claim 14, wherein the control module maintains a constant gain ratio between the image intensifiers.

23. A tissue abnormality detection system comprising:
   a light source for producing a beam of illumination light;
   an optical excitation filter that receives the illumination light and creates excitation light and reference light, the excitation light and reference light being directed onto a surface of interest;
   an imaging device including:
      at least one image forming optical assembly;
      an optical splitter that receives the fluorescence light and reflected reference light and directs the fluorescence light and reflected reference light into a fluorescence optical channel and a reflectance optical channel, the fluorescence optical channel including:
         an optical emission filter for passing light having selected wavelengths;
         an image intensifier tube that amplifies the light passed by the optical emission filter and produces an output image with the light passed;
      the reflectance optical channel including:
         an image intensifier tube that amplifies the light received in the reflectance optical channel and produces an output image with the light passed;
      a passive optical combiner that combines the images of the tissue produced with the fluorescence light and the reference light into a single image that can be viewed by a user; and
      a control module that controls the operation of the light source and the image intensifier tubes.

24. The tissue abnormality detection system of claim 23, wherein the reference light comprises the excitation light.

25. The tissue abnormality detection system of claim 23, wherein the light source produces both excitation light and reference light, and the reference light comprises light having a different wavelength than the excitation light and a different wavelength than that of the fluorescence emission which changes with disease.

26. The tissue abnormality detection system of claim 23, wherein the optical combiner comprises a dichroic mirror that is positioned to direct the output image from each optical channel into an eye of a user.

27. The tissue abnormality detection system of claim 23, wherein the system includes a pair of optical splitters which direct the light into multiple optical channels and produces a pair of combined output images for a binocular viewing.

28. The tissue abnormality detection system of claim 23, wherein the image intensifier tubes have long persistence phosphor screens.

29. The tissue abnormality detection system of claim 23, further comprising a camera positioned to capture the combined-output image onto an image sensor.

30. The tissue abnormality detection system of claim 29, wherein the image sensor is photographic film.

31. The tissue abnormality detection system of claim 29, wherein the image sensor is a digital imaging sensor.

32. The tissue abnormality detection system of claim 23, wherein the light source and image intensifier tubes are operated in a pulsed mode, synchronized and controlled by the control module.

33. The tissue abnormality detection system of claim 23, wherein the control module maintains a constant gain ratio between the image intensifiers.

* * * * *